(12) United States Patent
Singer

(10) Patent No.: US 7,832,021 B2
(45) Date of Patent: Nov. 16, 2010

(54) MEDICAL GLOVE WITH STETHOSCOPE PROTECTION

(76) Inventor: Jonathan Singer, 20 Wood Rd., Port Washington, NY (US) 11050

( * ) Notice: Subject to any disclaimer, the term of this patent is extended or adjusted under 35 U.S.C. 154(b) by 46 days.

(21) Appl. No.: 12/231,930

(22) Filed: Sep. 8, 2008

(65) Prior Publication Data
US 2009/0158499 A1 Jun. 25, 2009

Related U.S. Application Data

(63) Continuation-in-part of application No. 12/004,578, filed on Dec. 21, 2007, now abandoned.

(51) Int. Cl.
*A41D 19/00* (2006.01)
(52) U.S. Cl. .............. 2/161.7; 2/160; 2/161.1; 2/163
(58) Field of Classification Search ............... 2/16, 2/21, 158, 159, 160, 161.7, 163, 161.6; 294/25; 602/21, 22; 128/878, 879; D2/610, 616, D2/617
See application file for complete search history.

(56) References Cited

U.S. PATENT DOCUMENTS

| | | | | |
|---|---|---|---|---|
| 1,404,398 A * | 1/1922 | Lipson | ............. | 2/158 |
| 1,640,004 A * | 8/1927 | Lundblad | ............. | 224/217 |
| 2,554,991 A * | 5/1951 | Kramer | ............. | 2/159 |
| 2,847,676 A * | 8/1958 | Scott | ............. | 2/159 |
| 3,218,089 A * | 11/1965 | Marchand | ............. | 280/822 |
| 3,890,649 A * | 6/1975 | Diggins | ............. | 2/20 |
| 4,461,368 A * | 7/1984 | Plourde | ............. | 181/131 |
| 4,871,046 A * | 10/1989 | Turner | ............. | 181/131 |
| 5,138,718 A * | 8/1992 | Willard | ............. | 2/159 |
| 5,365,023 A * | 11/1994 | Lawton | ............. | 181/131 |
| 5,564,154 A * | 10/1996 | Cohn, III | ............. | 15/227 |
| 5,747,751 A * | 5/1998 | Weckerle et al. | ............. | 181/131 |
| 5,867,830 A * | 2/1999 | Chen | ............. | 2/161.1 |
| 5,987,645 A * | 11/1999 | Teaster | ............. | 2/159 |
| 6,186,957 B1 * | 2/2001 | Milam | ............. | 600/528 |
| 6,393,614 B1 * | 5/2002 | Eichelbaum | ............. | 2/160 |
| 6,467,568 B1 * | 10/2002 | Kemper | ............. | 181/131 |
| 6,481,766 B1 * | 11/2002 | May et al. | ............. | 294/1.3 |
| 6,511,111 B2 * | 1/2003 | Dooley | ............. | 294/1.3 |
| 6,745,403 B2 * | 6/2004 | Sajovic | ............. | 2/161.8 |
| 6,772,441 B2 * | 8/2004 | Lucas, Jr. | ............. | 2/161.1 |
| 2002/0100104 A1 * | 8/2002 | Hochmuth | ............. | 2/161.1 |
| 2004/0091678 A1 * | 5/2004 | Jordan | ............. | 428/192 |
| 2008/0235842 A1 * | 10/2008 | Patel et al. | ............. | 2/19 |

* cited by examiner

*Primary Examiner*—Gary L Welch
*Assistant Examiner*—Sally C Cline
(74) *Attorney, Agent, or Firm*—Amster, Rothstein & Ebenstein LLP

(57) ABSTRACT

A medical glove is provided for protection against the transmission of infectious agents. The glove comprises a glove body sized to tightly enclose a wearer's hand. The glove body has a palm portion and adjoining finger portions. A webbing adjoins two of the finger portions. The webbing is sized to receive a stethoscope head between the finger portions when the finger portions are separated. The glove is formed of an acoustically transmissive elastomeric material that is substantially non-porous and sufficiently thin to allow tactile sensitivity and dexterity.

11 Claims, 3 Drawing Sheets

MEDICAL GLOVE WITH STETHOSCOPE PROTECTION

CROSS-REFERENCE TO RELATED APPLICATION

This patent application is a continuation-in-part of U.S. patent application Ser. No. 12/004,578, filed Dec. 21, 2007 now abandoned, the contents of which are incorporated herein by reference in their entirety.

FIELD OF THE INVENTION

The present invention relates to medical gloves, and more particularly, to medical gloves that can be used to protect stethoscopes against the transmission of infectious agents.

BACKGROUND OF THE INVENTION

In the medical field, transmission of infectious agents and other contaminants is an ongoing concern. This issue has once again been pushed to the forefront with the incidence of nosocomial infections and antibiotic-resistant organisms, such as methicillin resistant *staphylococcus aureus* (MRSA).

To address the spread of infectious diseases in health care settings, hospitals have adopted sets of guidelines and best practices. For example, hospitals have implemented a set of "Universal Precautions" published by the Center for Disease Control (CDC) which includes precautions to minimize risk of infection with HIV by guarding against contact with blood and certain other bodily fluids known to carry HIV. Hospitals also have adopted "Body Substance Isolation," which is the practice of isolating all bodily substances (e.g., blood, urine, feces, tears, etc.) of individuals undergoing medical treatment to reduce the chances of transmitting nosocomial infections. Body Substance Isolation is similar in nature to the Universal Precautions, but goes further in isolating other substances not currently known to carry HIV.

The Universal Precautions and Body Substance Isolation urge the use of non-porous protective covers such as gloves, masks, gowns, and protective eyewear to reduce the risk of exposure to potentially infectious material. Further, the Occupational Safety and Health Administration (OHSA) requires health care workers to wear gloves when they come in contact with patients. These precautions are predominantly effective in protecting against the spread of infectious agents from the patient-to-health care worker and from health care worker-to-patient. In addition, health care workers are required to dispose of medical gloves and to dispose of or sterilize instruments in between patients in order to address patient-to-patient transfer of infections agents.

Health care workers use different types of medical gloves for different purposes. Medical gloves are classified as either examination gloves, which are typically used during non-sterile medical examinations of body surfaces and orifices, or surgical gloves, which are used in a sterile surgical environment. Medical gloves generally require greater feel and dexterity than non-medical gloves because they are used in precise and delicate medical procedures, and therefore have thinner walls than standard rubber gloves and are offered with more precise sizing.

However, despite these precautions, it has been found that health care workers are the primary cause for patient-to-patient transmission of nosocomial and antibiotic-resistant infections. The use of stethoscopes, in particular, is one area that has not been adequately addressed.

Typically, health care workers use personal or non-dedicated stethoscopes to examine each of their patients. Stethoscopes are used to assess heart rate and breathing, during which time the stethoscope head comes in direct contact with a patient's skin. Health care workers also make contact with the patient's skin with their gloves during an examination, and then their gloves come in contact various portions of the stethoscope.

Hospitals recommend sterilization of the entire stethoscope in between each patient examination, for example, by wiping off the entire stethoscopes with a 70% alcohol solution. However, this practice is not followed with great enough frequency in between each patient, and it is rare that the entire stethoscope is adequately sterilized.

As an alternative to sterilization, many different types of protective stethoscope covers and shields have been developed to prevent the stethoscope from coming into direct contact with patients. However, all of these protective stethoscope covers and shields have failed to gain acceptance for one reason or another, most often due to the additional effort required for application and removal, a lack of time, or simply general inconvenience.

For example, U.S. Pat. No. 4,461,368 to Plourde discloses a diaphragm shaped cover that is applied to the face of the stethoscope head. Plourde type covers are custom made to fit the shape of a particular stethoscope head. Because stethoscope heads come in a variety of designs and sizes, it would not be practical to stock the many different versions of the Plourde type cover that would be required to fit the variety of stethoscopes used by healthcare workers in a hospital.

U.S. Pat. No. 5,365,023 to Lawton discloses an elastomeric disk shaped cover applied over the face of the stethoscope head. Lawton type covers are more versatile and easier to apply than the Plourde type covers because they can be applied to a variety of types of stethoscopes. However, the health care worker is still required to spend additional time and effort when applying the cover, thereby causing additional inconvenience.

Stethoscope protective covers, such as disclosed in U.S. Pat. No. 4,871,046 to Turner, U.S. Pat. No. 5,269,314 to Kendall et al., U.S. Pat. No. 5,747,751 to Weckerle et al., U.S. Pat. No. 6,186,957 to Milam, and U.S. Pat. No. 6,467,568 to Kemper, involve the application of a loose fitting bag over the stethoscope head. These covers may also be more versatile and easier to apply than Plourde type covers, but the bags do not offer a good fit around the stethoscope head. The loose fit may interfere with the sound transmitted to the stethoscope and may be uncomfortable against the patient's skin. Furthermore, the health care worker is still required to spend additional time and effort when applying the cover, thereby causing additional inconvenience.

Therefore, there is a need for stethoscope protection that is effective, versatile, easy to apply, and convenient so that it will be used more frequently by health care workers.

SUMMARY OF THE INVENTION

According to one embodiment, a medical glove is provided for protection against the transmission of infectious agents. The glove comprises a glove body sized to tightly enclose a wearer's hand. The glove body has a palm portion and adjoining finger portions. A webbing adjoins two of the finger portions. The webbing is sized to receive a stethoscope head between the finger portions when the finger portions are separated. The glove is formed of an acoustically transmissive elastomeric material that is substantially non-porous and sufficiently thin to allow tactile sensitivity and dexterity.

According to one embodiment, the finger portions are adjoined by the webbing so as to form a single pocket for containing two or more fingers.

According to one embodiment, the webbing extends between two distinct finger portions.

According to one embodiment, the finger portions include at least an index finger portion and a middle finger portion, and the webbing adjoins the index finger portion and the middle finger portion.

According to one embodiment, the finger portions include at least a thumb portion and an index finger portion, and the webbing adjoins the thumb portion and the index finger portion.

According to one embodiment, the webbing includes a pocket adapted to receive at least a portion of a stethoscope head.

These and other features of this invention are described in, or are apparent from, the following detailed description of various exemplary embodiments of this invention.

BRIEF DESCRIPTION OF THE DRAWINGS

Exemplary embodiments of this invention will be described with reference to the accompanying figures.

DETAILED DESCRIPTION OF THE EXEMPLARY EMBODIMENTS

This invention is directed to a medical glove used to protect a stethoscope head from spreading infectious agents.

The glove may be comprised of an elastomeric material, such as latex, nitrile, vinyl, neoprene, polyisoprene, polyvinyl chloride (PVC), polyurethane, or the like. The elastomeric material may also be a combination of materials. The elastomeric material should be substantially non-porous and impervious to bodily fluids to prevent the spread of infectious agents, but also acoustically transmissive so not to interfere with the accuracy and level of sound transmitted to the stethoscope.

The glove should be manufactured to the medical glove standards set by the American Society for Testing and Materials (ASTM) and enforced by the U.S. Food and Drug Administration (FDA). The standards include approved materials, Acceptable Quality Level (AQL), and minimum requirements for palm wall thickness, finger wall thickness, tensile strength, elongation, and modulus. The minimum requirements are generally higher for sterile surgical gloves than for examination gloves.

Figure 1:
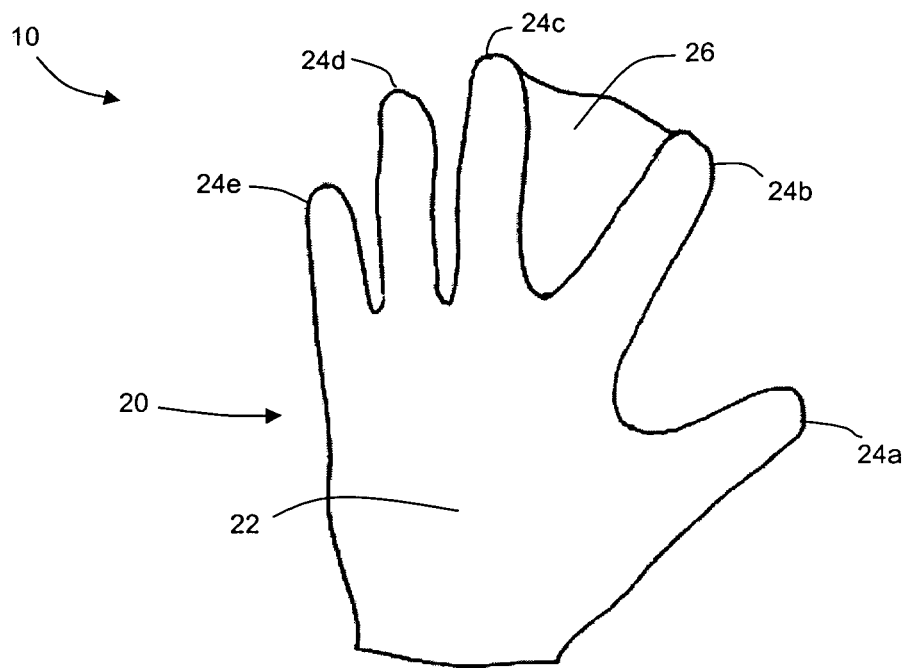
FIG. 1 is a top plan view of a medical glove according to an exemplary embodiment of the present invention.

Referring to FIG. 1, a medical glove 10 comprises a glove body 20. The glove body 20 includes a palm portion 22 and adjoining finger portions 24. The finger portions 24 typically include a thumb portion 24a, an index finger portion 24b, a middle finger portion 24c, a ring finger portion 24d, and a little finger portion 24e. The glove body 20 is sized to fit tightly over a wearer's hand.

Figure 5:
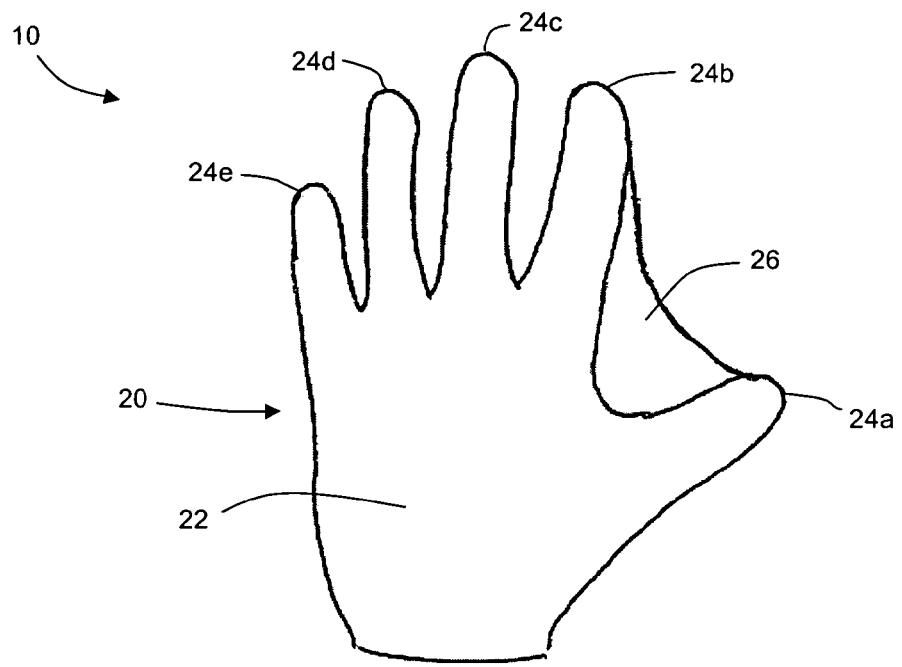
FIG. 5 is a top plan view of a medical glove according to another exemplary embodiment of the present invention.

A webbing 26 is formed to adjoin two of the finger portions 24. As illustrated in the exemplary embodiment of FIG. 1, the webbing 26 extends between the index finger portion 24b and the middle finger portion 24c. However, the webbing 26 can extend between any other adjoining finger portions 24, such as between the thumb portion 24a and the index finger portion 24b (see FIG. 5). Preferably, the webbing 26 is only formed between two of the finger portions 24 while the other finger portions 24 remain separate to retain maximal dexterity, however additional webbings may be formed between other finger portions 24 if desired.

Figure 6:
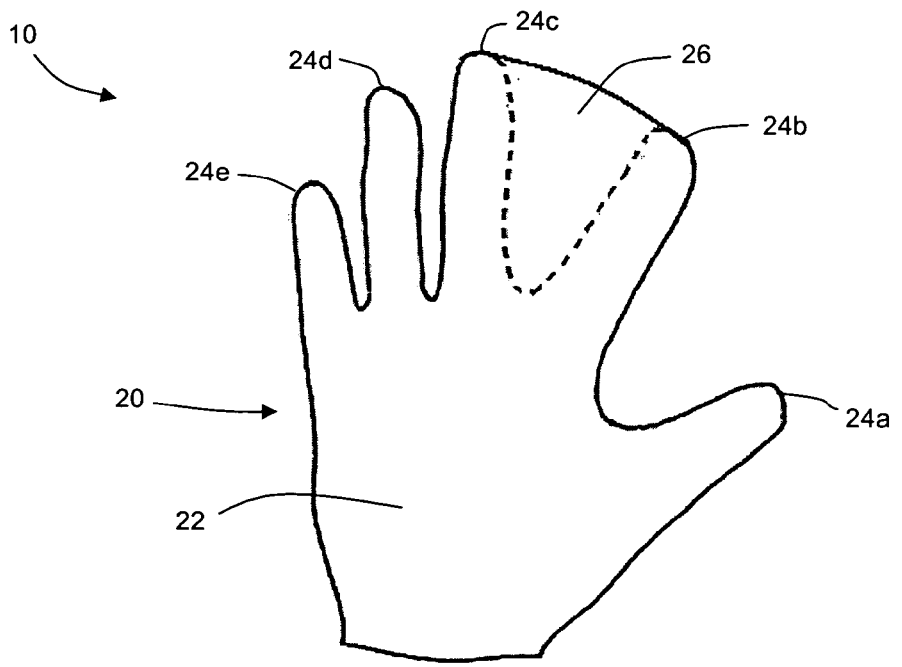
FIG. 6 is a top plan view of a medical glove according to another exemplary embodiment of the present invention.

As shown in FIG. 1, the webbing 26 may be formed as a web extending between two separate and distinct finger portions 24. However, as shown in FIG. 6, the finger portions 24 may be adjoined by the webbing 26 so as to create a single pocket for containing two or more fingers.

The webbing 26 may extend from the base toward the tip of the finger portions 24. The webbing 26 may extend fully or partially toward the tip of the finger portions 24. When the finger portions 24 are separated apart, the webbing 26 is stretched to provide a substantially smooth surface. When the finger portions 24 are brought close together the webbing 26 returns to a contracted state.

Figure 2:
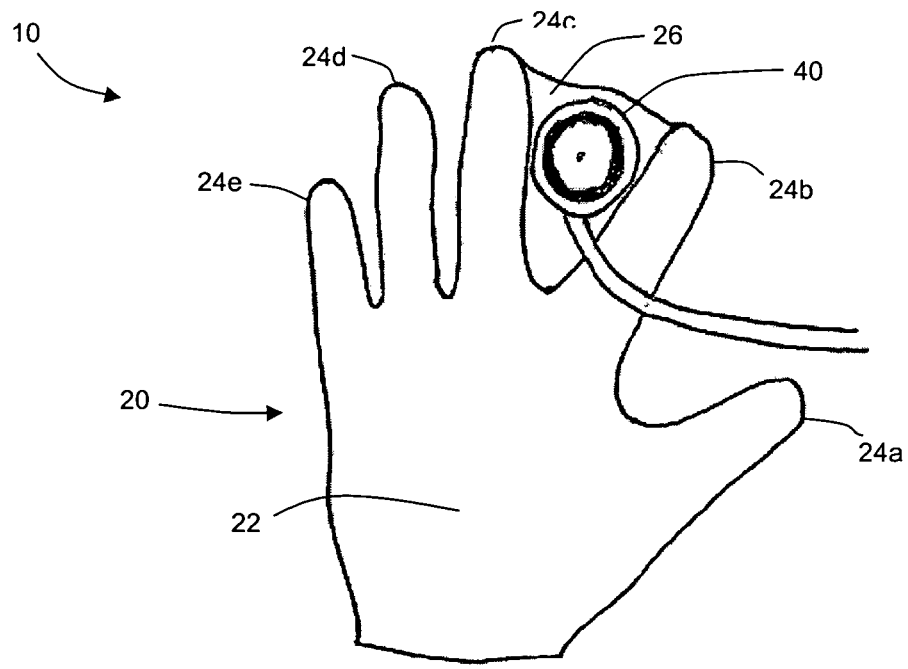
FIG. 2 is a top plan view of the glove of FIG. 1 shown with a stethoscope head placed against the webbing.
Figure 3:
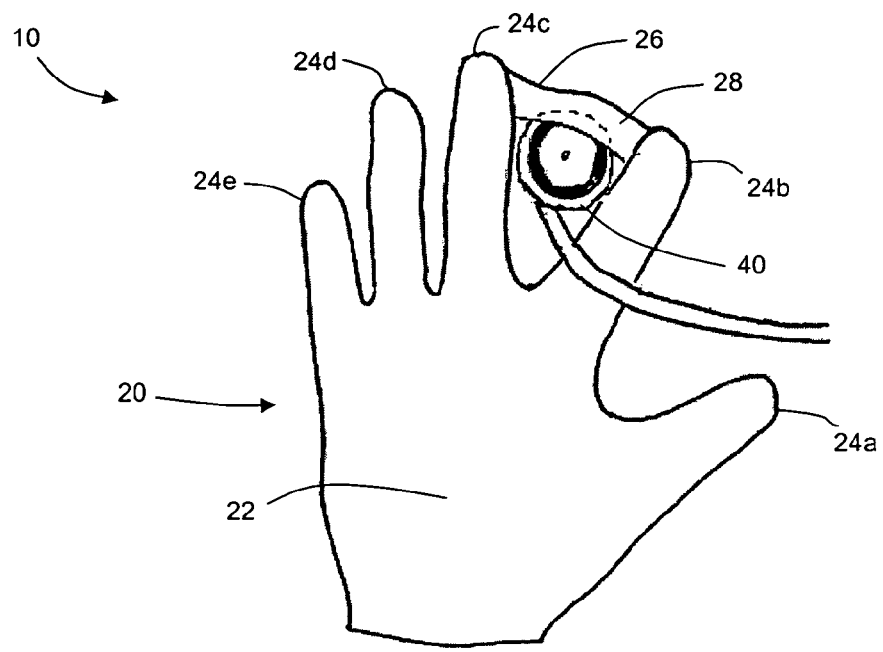
FIG. 3 is a top plan view of the back-side a medical glove according to another exemplary embodiment of the present invention, shown with a stethoscope head inserted into a pocket in the webbing.
Figure 4:
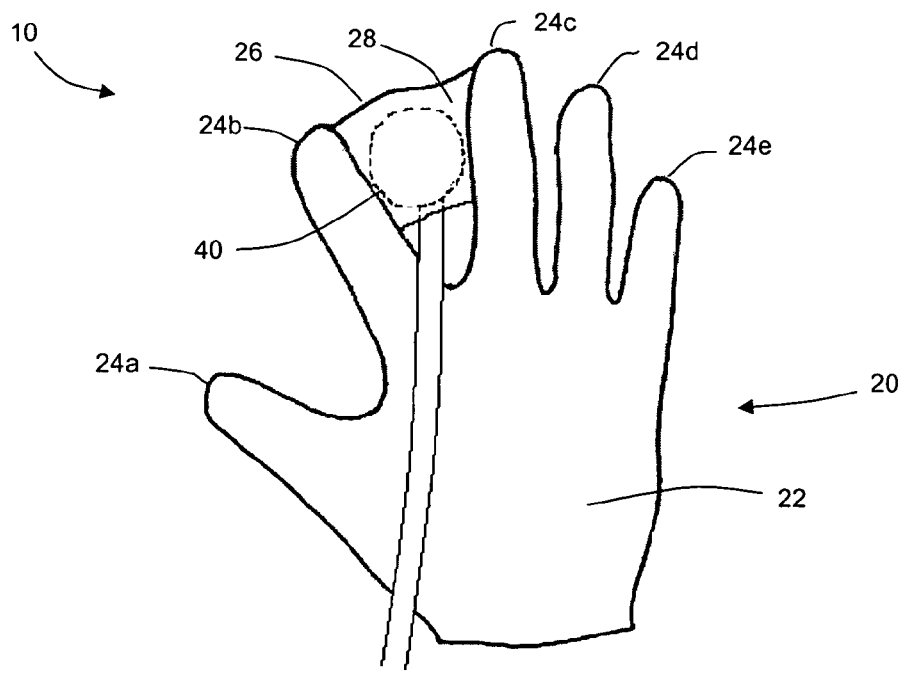
FIG. 4 is a top plan view of the palm-side of a medical glove according to another exemplary embodiment of the present invention, shown with a stethoscope head inserted into a pocket in the webbing.

The webbing 26 is sized to receive a stethoscope head 40 when the webbing 26 is stretched (see FIG. 2). Stethoscope heads 40 come in different sizes, but are typically about 4 cm to 5 cm in diameter. The webbing 26 can also include a pocket or flap 28 to receive at least a portion of the stethoscope head 40 (see FIGS. 3-4). The pocket or flap 28 may assist in holding the stethoscope head 40 in place. The pocket or flap 28 may be located on the back side (see FIG. 3) or the palm side (see FIG. 4) of the webbing 26.

The glove 10 should have a wall thickness sufficient to guard against rips and tears, but should also be sufficiently thin to retain dexterity and feel. For example, the glove 10 may have a wall thickness between about 0.01 mm to 0.40 mm. Preferably, glove 10 may have a wall thickness of about 0.05 mm to 0.20 mm. The minimum wall thickness permitted by the FDA is 0.05 mm for examination gloves and 0.10 mm for surgical gloves. The webbing 26, in particular, should be relatively thin when stretched to minimize distortion in the sound transmitted to the stethoscope.

In use, a health care worker wearing the glove 10 separates the two of their fingers between which the webbing 26 is connected, for example, their index finger and middle finger as seen in FIG. 2. Accordingly, the finger portions 24b and 24c are separated and the webbing 26 is stretched to form a substantially smooth surface. The health care worker then places the stethoscope head 40 against the webbing 26 and presses against a patient's body. The webbing 26 forms a protective barrier between the stethoscope head 40 and the patient.

Accordingly, the medical glove of the present invention will prevent stethoscope heads from coming in direct contact with a patient's skin, thereby providing protection against the transmission of infectious agents. Further, since medical gloves are required to be used by all health care workers, a medical glove that can also be used to protect a stethoscope during examination of a patient will used more frequently than other currently available methods of stethoscope protection because of its convenience.

Now that exemplary embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

What is claimed is:

1. Protective equipment for a stethoscope, comprising:
   a medical glove for guarding against the transmission of infectious agents, said glove formed of a substantially non-porous and fluid impervious elastomeric material sized to tightly enclose a wearer's hand having a wall thickness of about 0.01 mm to 0.40 mm and provides tactile sensitivity, dexterity, and acoustic transmissivity, said glove comprising:
   a palm portion,
   adjoining finger portions, and
   a webbing adjoining two of said finger portions; and
   wherein said webbing material provides acoustic transmissivity to a stethoscope.

2. The protective equipment of claim 1, wherein said webbing is further comprising a flap forming a stethoscope retaining pocket enclosure.

3. The protective equipment of claim 1, wherein said finger portions are adjoined by said webbing forming a single region for containing two or more fingers of the wearer.

4. The protective equipment of claim 1, wherein said webbing extends between two distinct finger portions.

5. The protective equipment of claim 1, wherein said finger portions include at least an index finger portion and a middle finger portion, and said webbing adjoins said index finger portion and said middle finger portion.

6. The protective equipment of claim 1, wherein said finger portions include at least a thumb portion and an index finger portion, and said webbing adjoins said thumb portion and said index finger portion.

7. The protective equipment of claim 1, wherein said glove has a wall thickness of about 0.05 mm - 0.20 mm.

8. The protective equipment of claim 1, wherein the elastomeric material comprises at least one of latex, nitrile, vinyl, neoprene, polyisoprene, polyvinyl chloride polymer, and polyurethane.

9. The protective equipment of claim 1, wherein the glove is an examination glove.

10. The protective equipment of claim 1, wherein the glove is a surgical glove.

11. Protective equipment for a stethoscope, comprising:
    a medical glove for guarding against the transmission of infectious agents, said glove formed of a substantially non-porous and fluid impervious elastomeric material sized to tightly enclose a wearer's hand having a wall thickness of about 0.01 mm to 0.40 mm and provides tactile sensitivity, dexterity, and acoustic transmissivity, said glove comprising:
    a palm portion,
    adjoining finger portions, and
    a webbing adjoining two of said finger portions;
    wherein said webbing material provides acoustic transmissivity to a stethoscope; and wherein said finger portions include at least an index finger portion and a middle finger portion, and said webbing adjoins said index finger portion and said middle finger portion.

* * * * *